US011583996B2

(12) United States Patent
Skertich et al.

(10) Patent No.: US 11,583,996 B2
(45) Date of Patent: Feb. 21, 2023

(54) GRIPPING AID FOR THE MANUALLY IMPAIRED

(71) Applicants: Celine Rosati Skertich, Western Springs, IL (US); Linda Merry, Elmhurst, IL (US)

(72) Inventors: Celine Rosati Skertich, Western Springs, IL (US); Linda Merry, Elmhurst, IL (US)

( * ) Notice: Subject to any disclaimer, the term of this patent is extended or adjusted under 35 U.S.C. 154(b) by 109 days.

(21) Appl. No.: 16/372,070

(22) Filed: Apr. 1, 2019

(65) Prior Publication Data

US 2020/0306951 A1 Oct. 1, 2020

(51) Int. Cl.
*B25J 1/04* (2006.01)
*B25J 15/00* (2006.01)

(52) U.S. Cl.
CPC ............. *B25J 1/04* (2013.01); *B25J 15/0033* (2013.01)

(58) Field of Classification Search
CPC ......... B25J 1/04; B25J 15/0033; B25B 13/52; A61F 4/00
See application file for complete search history.

(56) References Cited

U.S. PATENT DOCUMENTS

| | | | | |
|---|---|---|---|---|
| 2,416,030 | A * | 2/1947 | Vesper | A61F 2/58 623/59 |
| 3,972,628 | A * | 8/1976 | Stevers | B43L 15/00 401/48 |
| 4,511,272 | A * | 4/1985 | Brown | B43L 15/00 401/48 |
| 5,212,900 | A * | 5/1993 | Perry | A01K 97/10 224/222 |
| 6,394,516 | B1 * | 5/2002 | Zhuravsky | A47G 21/08 224/218 |
| 8,474,470 | B2 * | 7/2013 | Albertyn | A61H 3/02 135/71 |
| 9,987,189 | B2 * | 6/2018 | Dropsho | A61H 3/0288 |
| 2013/0270850 | A1 * | 10/2013 | Fan | A45F 5/00 294/137 |

* cited by examiner

*Primary Examiner* — Stephen A Vu
(74) *Attorney, Agent, or Firm* — UIC Law School Patent Clinic

(57) ABSTRACT

An apparatus for manually impaired individuals. The apparatus includes a top element having a base and at least two pairs of arms extending outwardly from the base. The base includes a first aperture and a second aperture. The apparatus further includes a handle connecting to the top element at a distal end of the top element. The handle includes an end part. The end part includes a third aperture and a slot connected by a "V" shaped portion. The apparatus further includes a restraint having a first end securing at an interior of the handle via the first aperture of the base and a second end of the restraint exposed outside the handle.

20 Claims, 13 Drawing Sheets

GRIPPING AID FOR THE MANUALLY IMPAIRED

CROSS-REFERENCE TO RELATED APPLICATIONS

This is a US nonprovisional application of U.S. provisional application, Ser. No. 62/761,773, filed on Apr. 5, 2018, whose disclosure is incorporated by reference in its entirety herein.

TECHNICAL FIELD

The invention relates to hand aids for individuals with manual impairments where a person is unable to adequately grasp, hold or manipulate functional tools such as stylus, paintbrush, glue stick, marker, pencil, pen, utensil of a wide variety of sizes without slippage.

RELATED ART

Hand aids for manually impaired individuals tend to be designed for specific tasks or specific supported implements. When supporting nonspecific implements, those hand aids require that the implement be modified in such away so as to fit the hand aid. Many adaptive devices and universal cuffs are unable to maintain the tool in a stable position. Slippage and limited ability to adapt to a variety of sizes and shapes are consistent limitations. It would be beneficial if the hand aid could support a large variety of implements at a position most suited to the individual, the function and the ergonomics of the task.

SUMMARY

Aspects of the invention comprise a device that will hold an implement for manually impaired persons. It is shaped in a way to orient itself comfortably in either hand of the manually impaired person. The supported implement need not to be modified to fit this device according to embodiments of the invention. The supported implement is firmly held in place against four high friction supports by a restraining device that can also act as a hand support if so desired, supporting the hand aid in the user's hand.

A basic problem arises with an invention of this type. The range of motion, integrity of the arches that support the hand, relative position and size of the impaired hand can vary a good deal from one person to the next. This raises the need to be able to customize the device as needed. To accomplish this, the portion of the device that needs customizing is created by a 3D CAD computer program and produced by a 3D printer compatible with the 3D CAD output. The 3D CAD output is a mathematical model determining where such things as size, handle shape, inclusion of hand support, relative angles between the handle and the implement support are determined by constants. A computer program can be easily written with these constants as an input thereby allowing customization of the device at little or no added cost. These 3D CAD models can be converted to the appropriate files for mold manufacturing.

BRIEF DESCRIPTION OF THE DRAWINGS

Some embodiments of the present invention are illustrated as an example and are not limited by the figures of the accompanying drawings.

DETAILED DESCRIPTION

Figure 1:
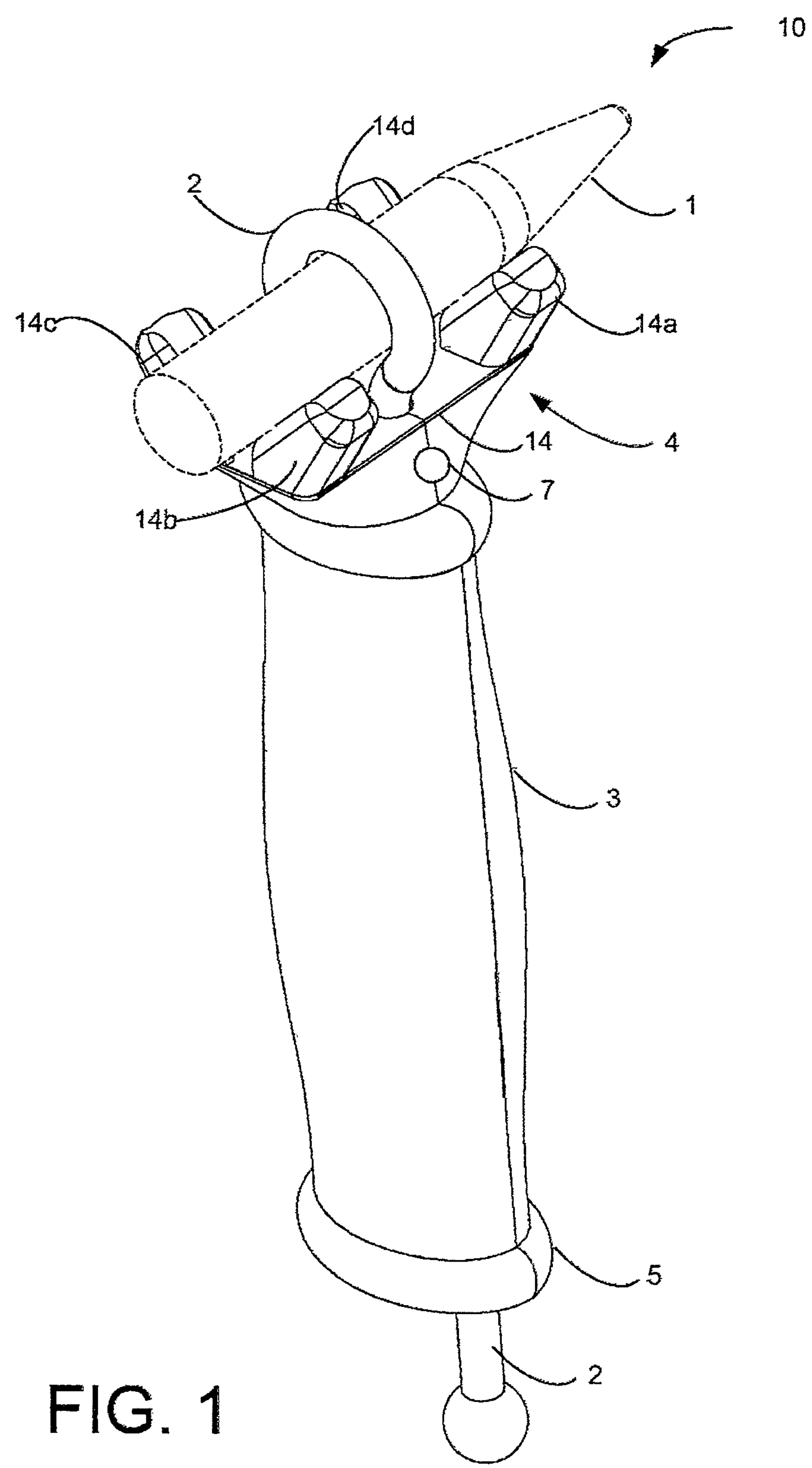
FIG. 1 is a perspective view with a supported implement and without a hand supporting feature according to one embodiment of the invention.

The terminology used herein is for the purpose of describing particular embodiments only and not intended to be limiting of the invention. When referring to the Figures, like numerals and their subsets indicate like or corresponding parts throughout the views.

The invention provides for two embodiments, FIGS. 1-4 illustrate an embodiment with no hand support and FIGS. 5-8 illustrate another embodiment with a hand support. Each embodiment includes two basic parts. For example, a gripping aid 10 may include an implement restraint 2, which in this case may be a flexible, elastic cord. The gripping aid 10 further includes a handheld implement support top 4, a handle 3, and an end part 5. In one embodiment, the support top 4 includes a base 14 and two pairs of arms. In one embodiment, the arms 14*a-d* may be to hold or engage an implement 1. In one embodiment, the arms 14*a-d* may include various three-dimensional geometric shapes, such as a combination of prisms, cuboid, etc. In one example, as illustrated in figures of this application, each of the four arms 14*a*-14*d* may include a tip with a smaller cross-section area than that of the end of each of the four arms 14*a-b*. It is to be understood, however, that other geometric shapes may be used for the base 14 and the arms 14*a-d* without departing from the scope or spirit of embodiments of the invention.

In the embodiment of a hand support, the gripping aid 10 may include a second end part 6 for housing the hand support 8 (to be further discussed in FIGS. 5-8). In one embodiment, the implement restraint 2 and various elements (e.g., the arms 14*a-d*) of the gripping aid 10 may be used to contain the implement 1. As a simplistic illustration, the implement 1 is shown as a bullet shaped pointer.

Figure 2:
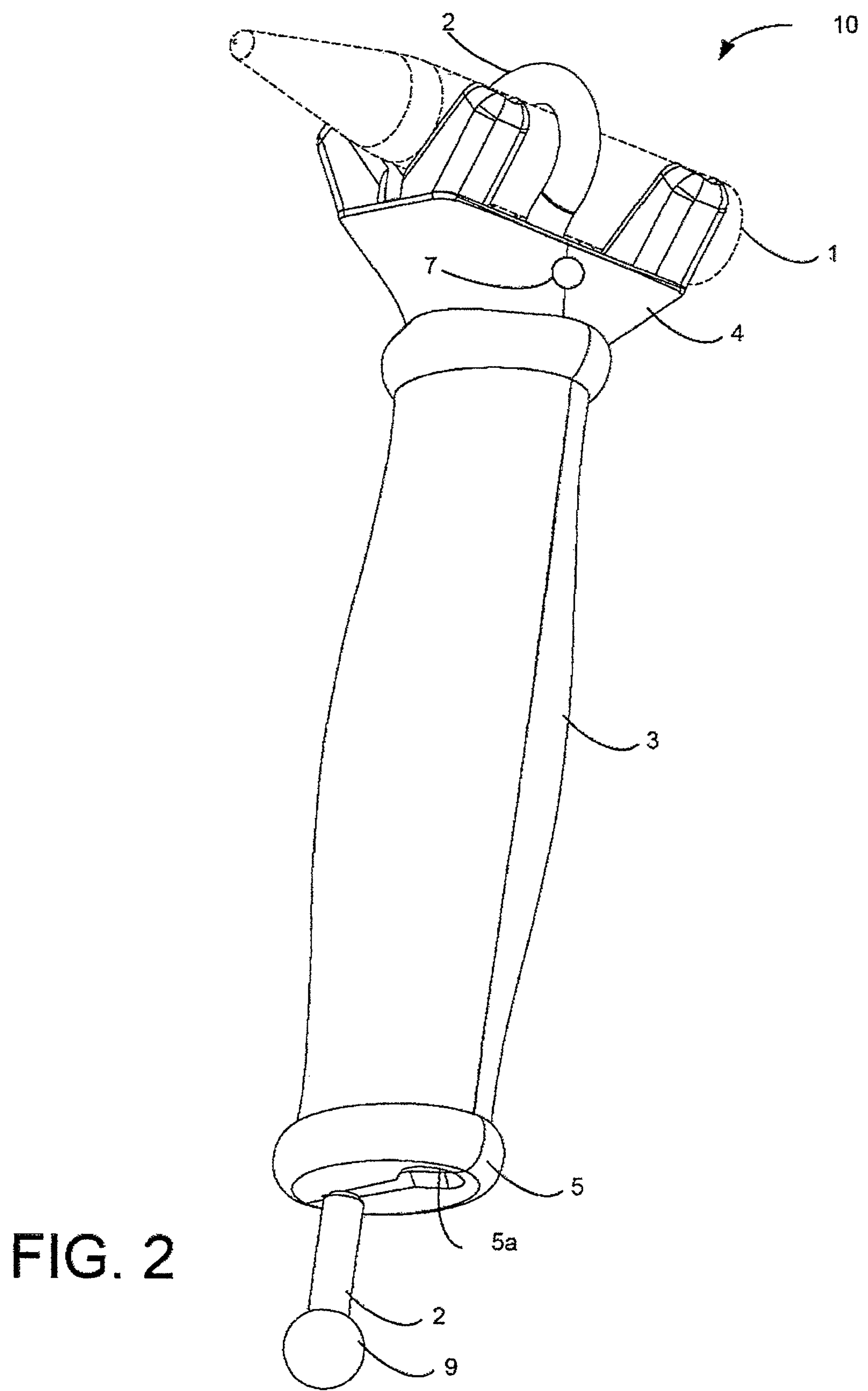
FIG. 2 is another perspective view of FIG. 1 according to one embodiment of the invention.

In one embodiment, FIGS. 1-2 show the implement 1 captured between the restraint 2 and the support top 4. In one embodiment, the restraint 2 has one end held in the support top 4 by being inserted into an aperture 4*a* (see also FIG. 3) and captured by a restraining screw 7 at an interior spot. The other end of the restraint 2 leads thru an aperture 4*b* (see also FIG. 3), thru the interior of the support handle 3 and out the support bottom aperture 5*a* where it is captured in a "V" shaped portion 5*b* of the aperture 5*a* (see also FIG. 15) so as form a space to receive the implement 1 and to keep the implement 1 tight and not allow the implement 1 to move. In another embodiment, the restraint 2 may be further moved to a slot 5*c* to lock the restraint 2 in place or to further restrict movement of the restraint 2. (see also FIG. 9). In one embodiment, the restraint 2 may include a protuberance such as a knob 9 for a user to grab or otherwise secure the restraint 2 easier. It should be understood that other configurations to the end of the cord may be utilized without departing from the scope or spirit of the embodiments of the invention.

Figure 3:
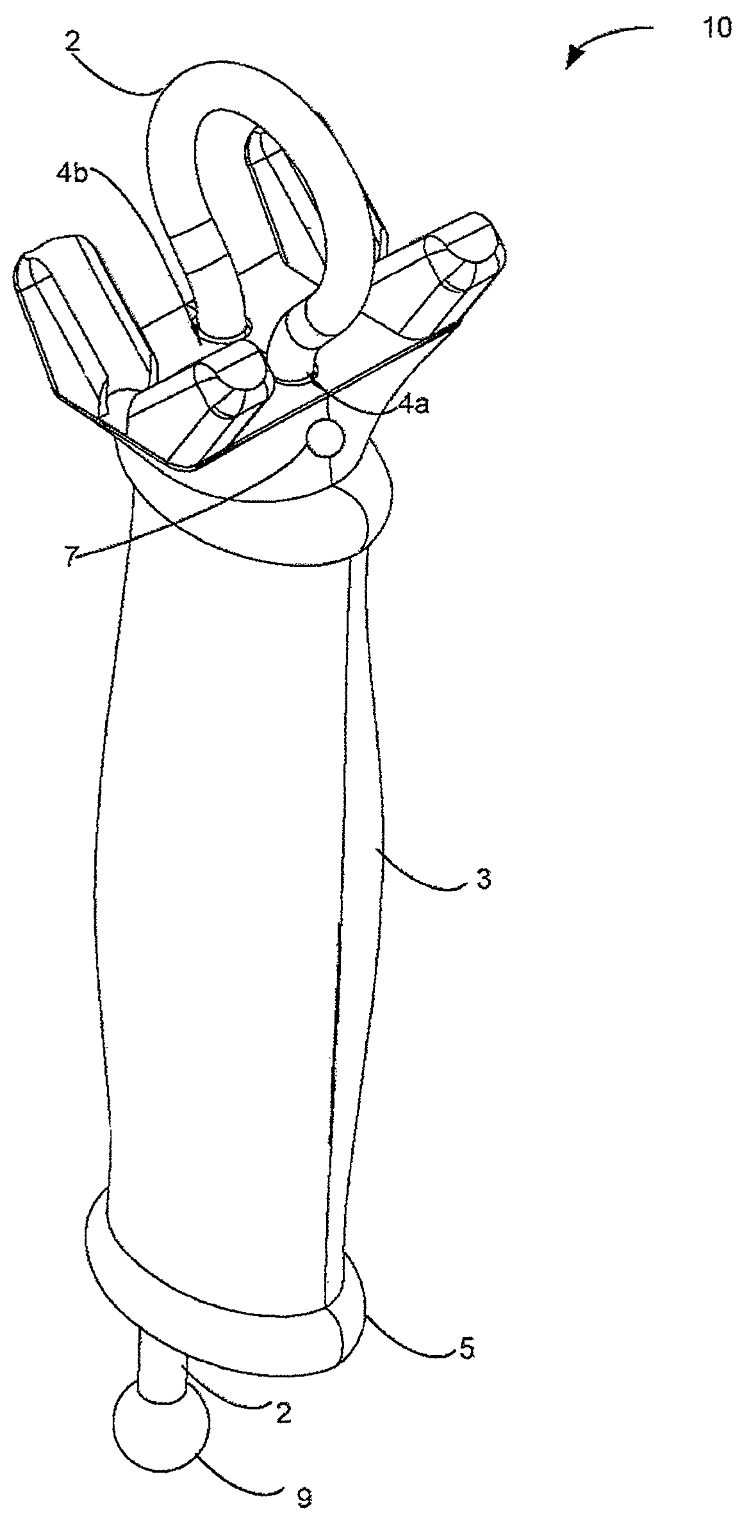
FIG. 3 is a perspective view without a supported implement and without a hand supporting feature according to one embodiment of the invention.
Figure 4:
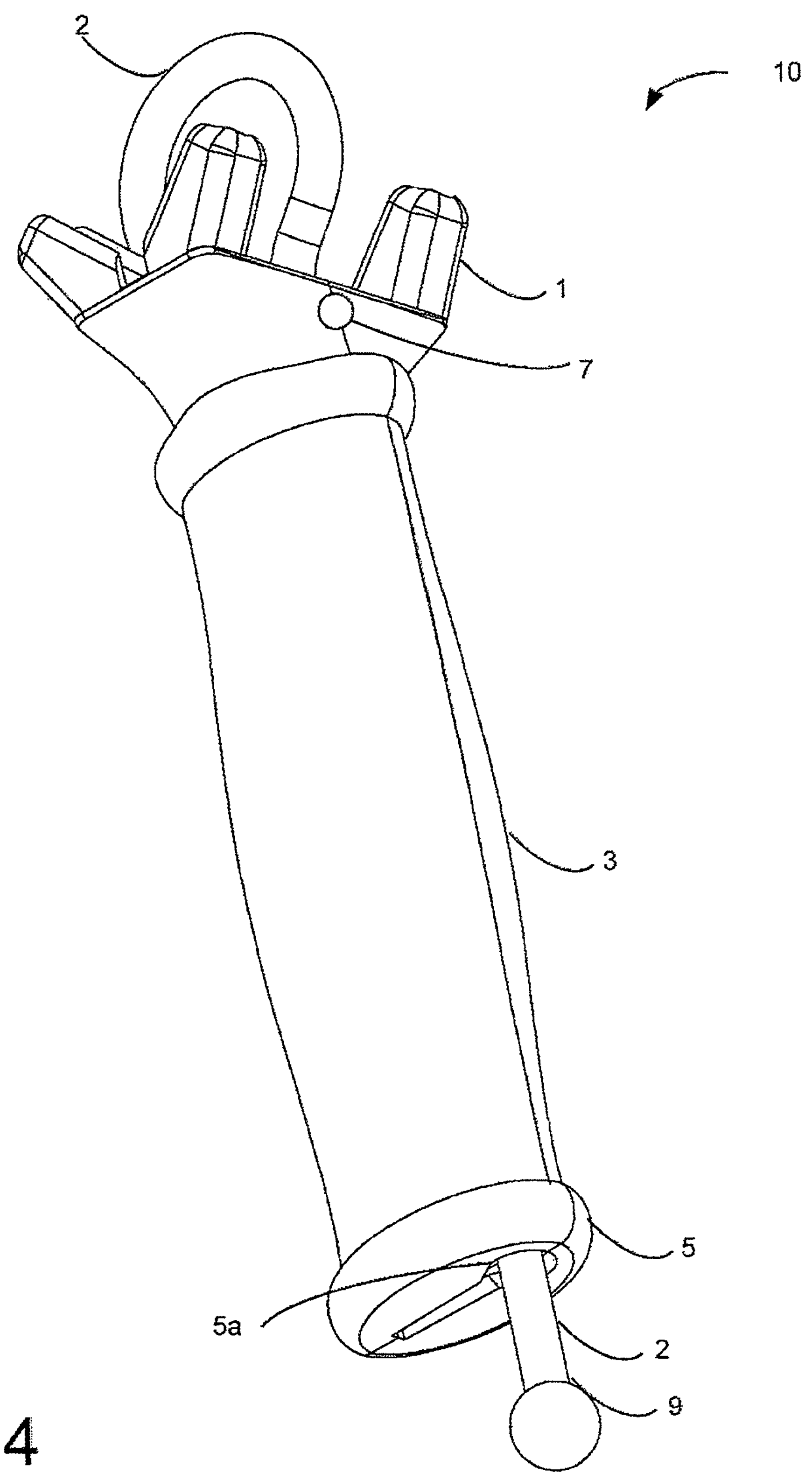
FIG. 4 is another perspective view of FIG. 3 according to one embodiment of the invention.

FIGS. 3-4 show another embodiment of the invention. In this example, the gripping aid 10 may be ready to receive an implement, such as the implement 1. Note that the restraint 2 may be loosen increase a size of the loop created between the apertures 4*a* and 4*b* to receive an implement to be easily placed on the support top 4 and can be tightened with one hand at the support bottom 5 through the aperture 5*a*. In another embodiment, the protuberance such as the knob 9 may prevent the restraint 2 from retracted into the body 3. As such, protuberance such as the knob 9 may be a sphere with a circumference that is bigger than that of the aperture 5*a*. In another embodiment, the one hand of the user or another person may slide the restraint 2 from the aperture 5*a* to the slot 5*c* to tighten and secure the implement 1.

Figure 5:
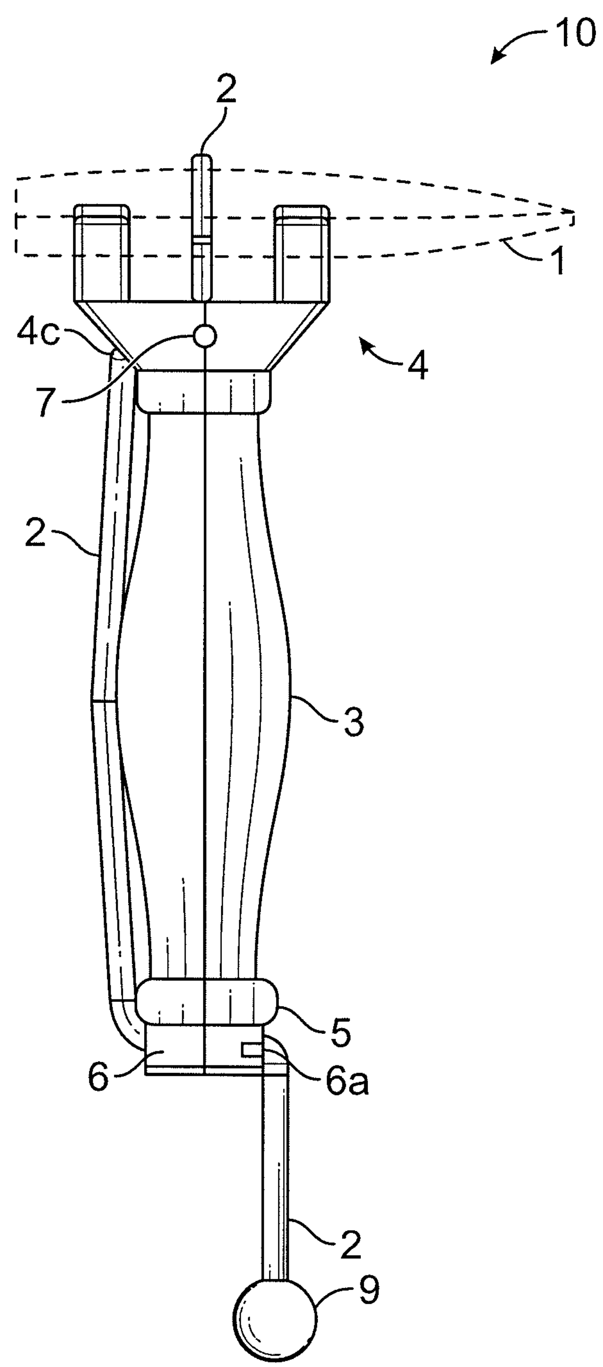
FIG. 5 is a side view with a supported implement and with a hand supporting feature according to one embodiment of the invention.
Figure 6:
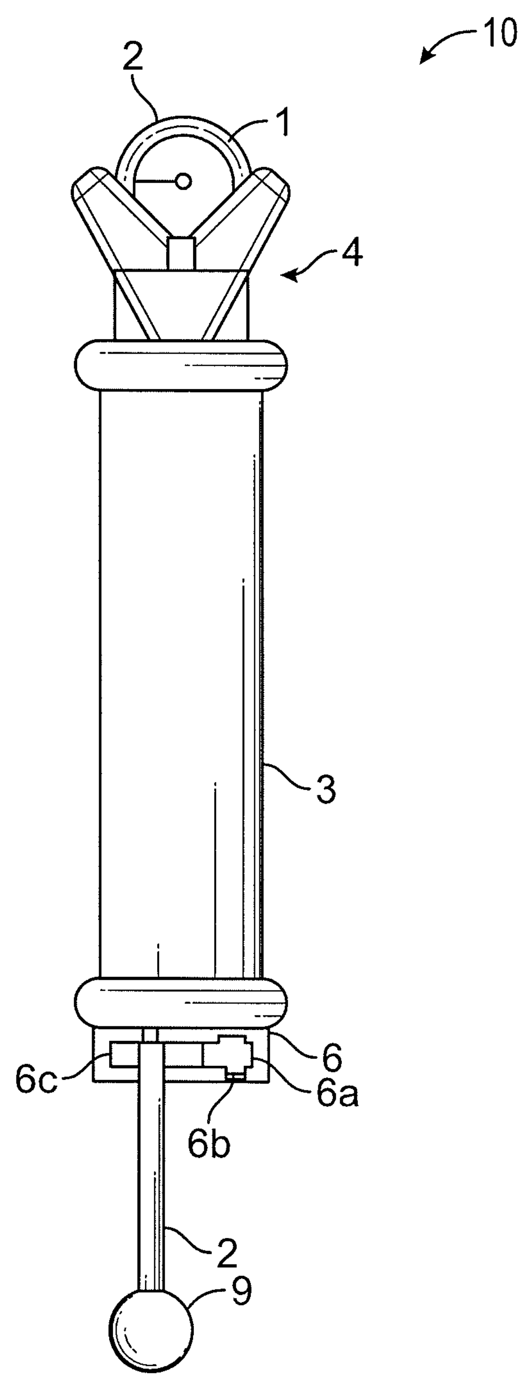
FIG. 6 is another side view of FIG. 5 according to one embodiment of the invention.

FIGS. 5-6 show another embodiment of the gripping aid 10. In this embodiment, the implement 1 captured between the restraint 2 and the support top 4 where the restraint 2 has one end held in the support top 4 by being inserted into the aperture 4*a* and captured by the restraining screw 7 at the interior spot.

In this embodiment, the other end of the restraint 2 leads thru the aperture 4*b* and out to an aperture 4*c* at the base 14 of the top 4. As such, a portion of the restraint 2 is on the exterior of the handle 3 (as compared to being in the interior of the handle 3 in the embodiment shown in FIGS. 1-4). The restraint 2 then leads straight down the outside of the handle 3 to support a bottom 6 via an aperture 6*a* and out to an aperture 6*b* where it is captured in a "V" shaped portion 6*c* of that aperture so as to keep the instrument 1 tight and not allow the implement 1 to move freely between the four arms 14*a-d*. See also FIG. 16. In one embodiment, the bottom 6 may be an extension of the end part 5. In another embodiment, the restraint 2 may be further moved to a slot 6*d* to lock the restraint 2 in place or to further restrict movement of the restraint 2. Note that this action also makes the restraint 2 tighten against handle 3 so that, if a human hand was inserted between the restraint 2 and the handle 3, this configuration would act as a hand support helping to hold the gripping aid 10 in a manually impaired hand.

Figure 7:
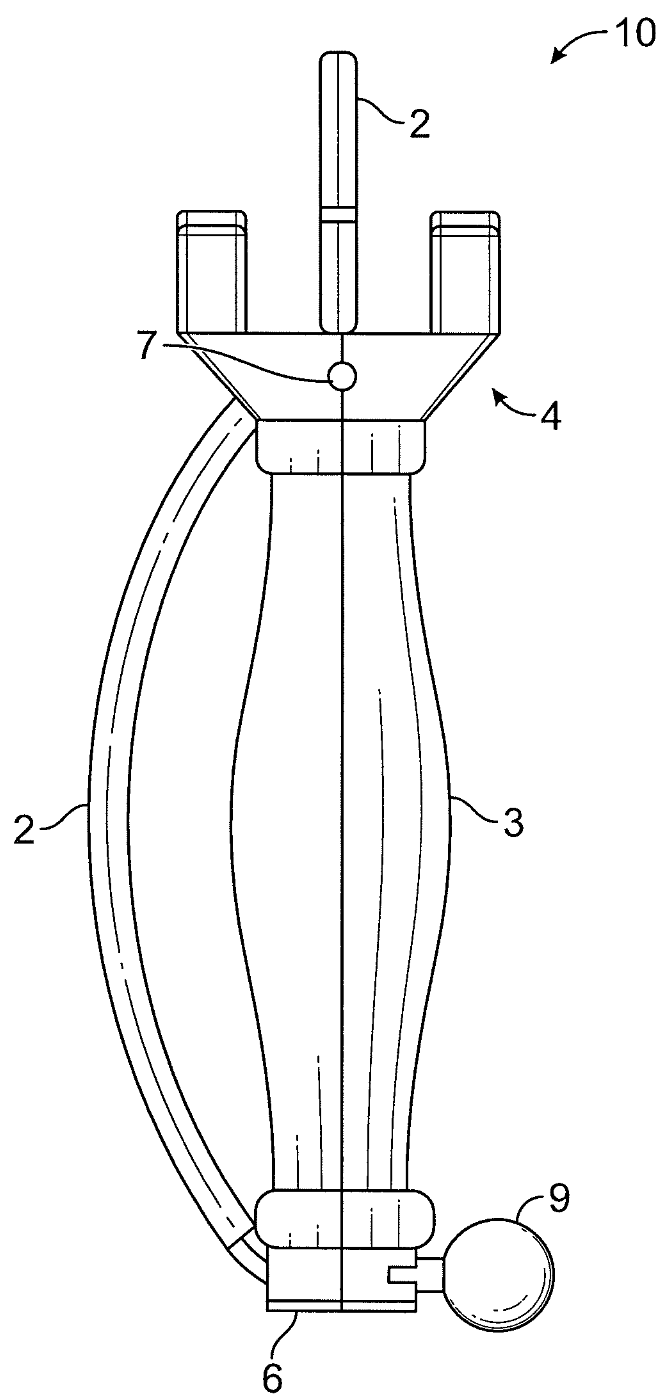
FIG. 7 is another side view without a supported implement and with a hand supporting feature according to one embodiment of the invention.
Figure 8:
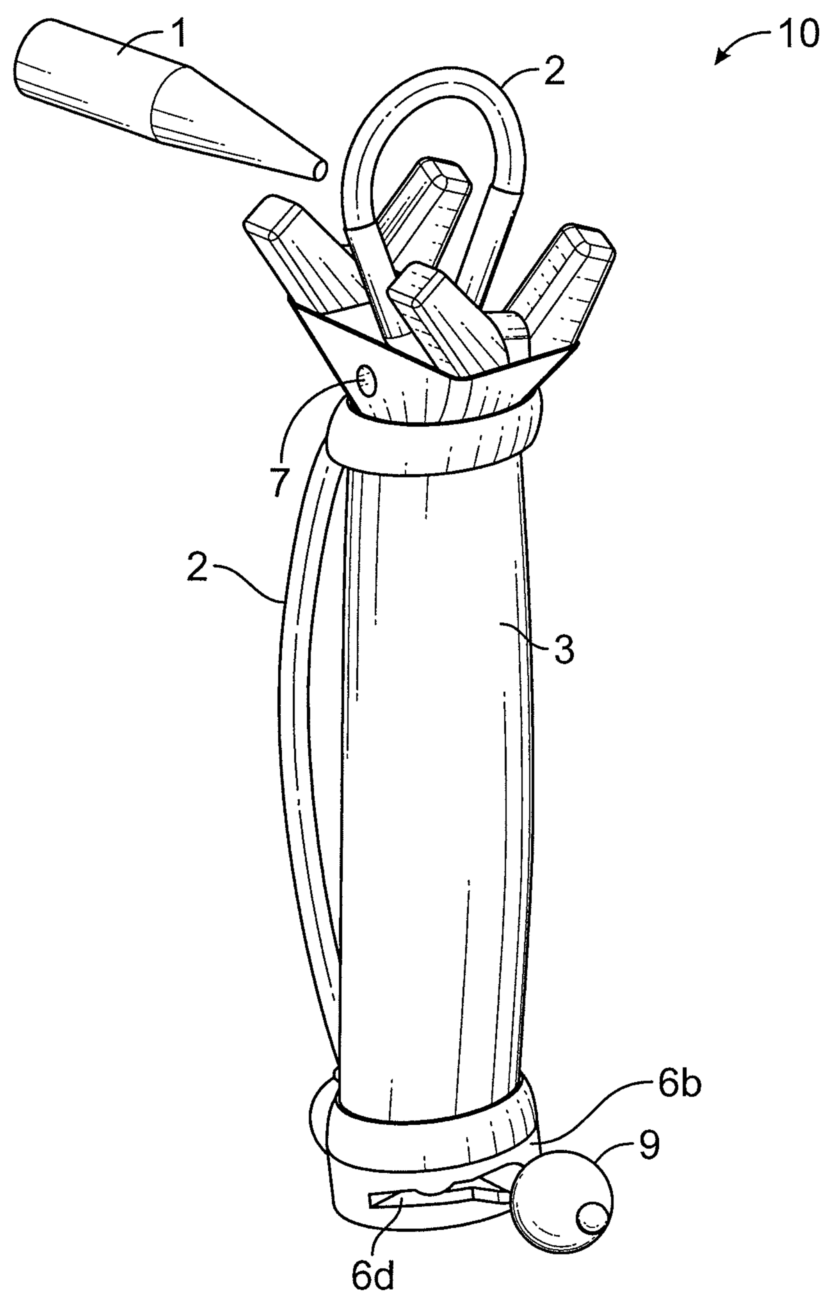
FIG. 8 is a perspective view of FIG. 7 according to one embodiment of the invention.
Figure 9:
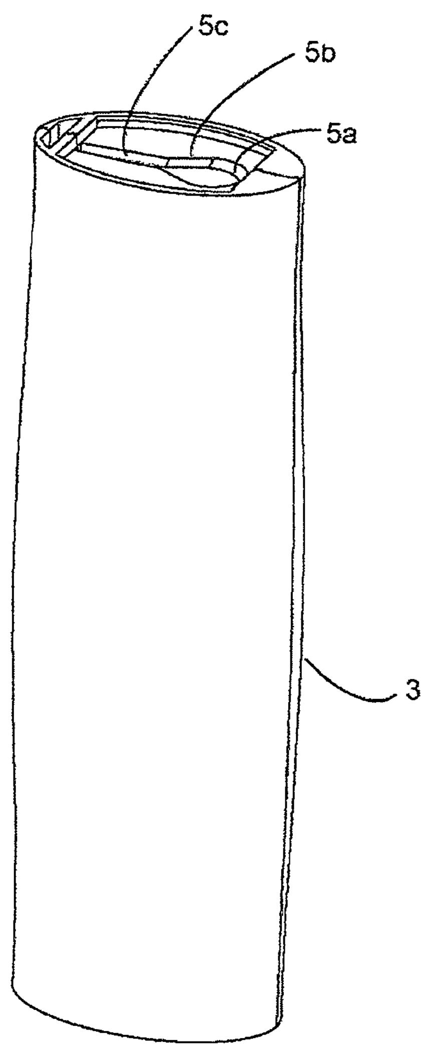
FIG. 9 is a perspective view of an end of a handle without a hand supporting feature according to one embodiment of the invention.
Figure 10:
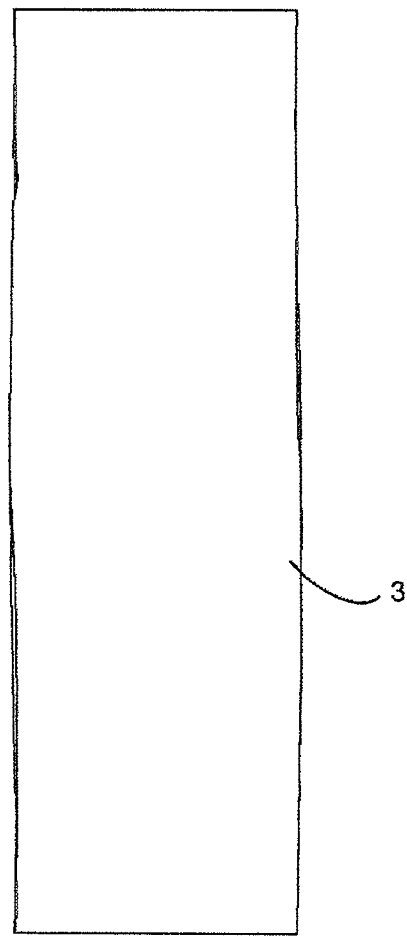
FIG. 10 is a front view of a handle according to one embodiment of the invention.
Figure 11:
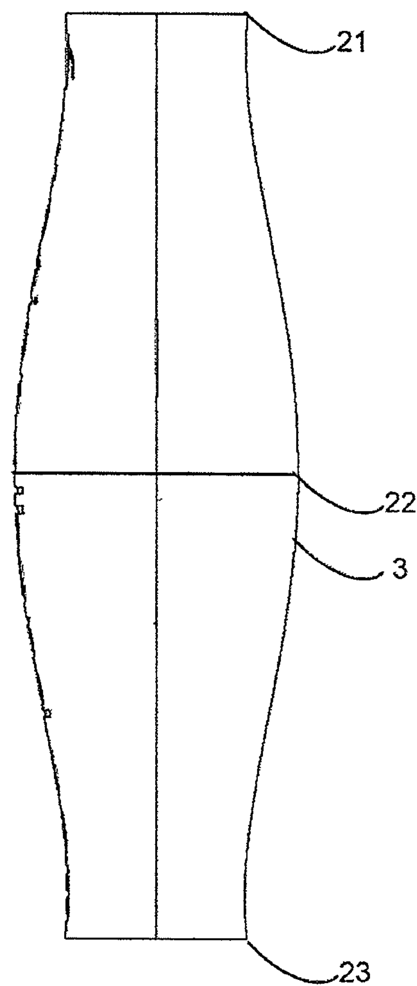
FIG. 11 is a side view of a handle according to one embodiment of the invention.

FIGS. 7-8 show the invention ready to receive an implement. In these illustrations, the restraint 2 at the exterior of the handle 3 is relaxed, as well as the portion between holes 4*a* and 4*b*. As also illustrated in FIG. 8, the protuberance such as a knob 9 appears to be closer to the aperture 6*b* of the bottom 6. In one embodiment, the restraint 2 allows the implement 1 to be easily placed between the support top 4 and the users hand has plenty of room for insertion between the restraint 2 and the handle 3 so that tightening the restraint at the support bottom 6*b* captures the implement 1 and at the same time hold the invention in the user's hand FIGS. 9-11 show three views of the handle 3. In one embodiment, FIG. 9 illustrates a perspective view showing more details of the end part 9, which have been described above. FIG. 10 is a view perpendicular to the X axis of the handle 3 as shown in FIG. 1. FIG. 11 is a view perpendicular to the Y axis as shown in FIG. 1. In one embodiment, the handle 1 may be defined by three ellipses (as of cross-sectional), one of each located at 21, 22, and 23. Ellipses located at 21 and 23 are shown as being the same with the ellipse located at 22 being the same as those at 21 and 23 on the X axis but larger on the Y axis and midway between the ellipses at 21 and 23. In one embodiment, this is thought to be the best shape to keep the gripping aid oriented correctly, support the arches of the user's hand and allow it to be ambidextrous. However, it is to be understood that other shapes of the handle, whether ergonomically designed or not to the hand of a human, may be designed without departing from the scope or spirit of embodiments of the invention.

Figure 12:
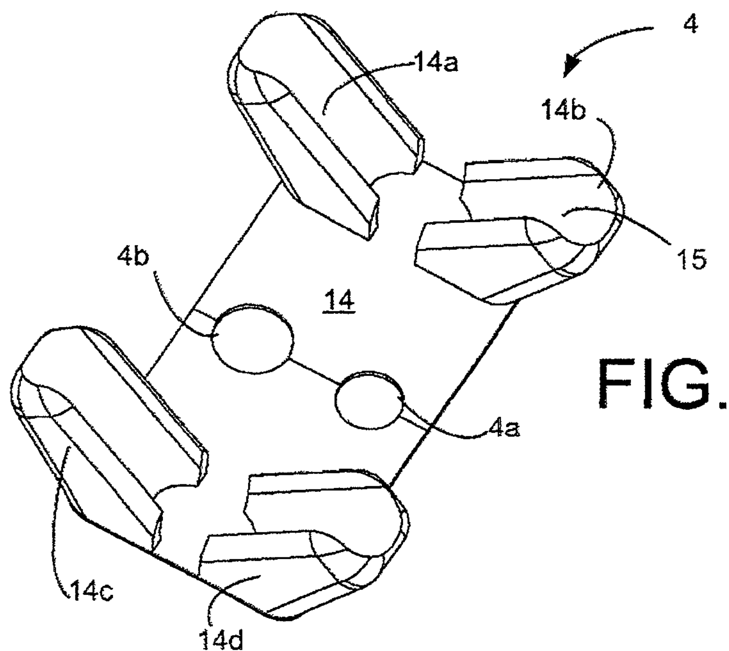
FIG. 12 is a perspective view of a support top without anti-slip inserts according to one embodiment of the invention.
Figure 13:
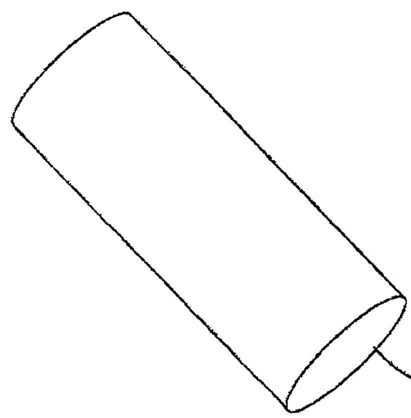
FIG. 13 is a view of an anti-slip element to be attached on the supported implement according to one embodiment of the invention.
Figure 14:
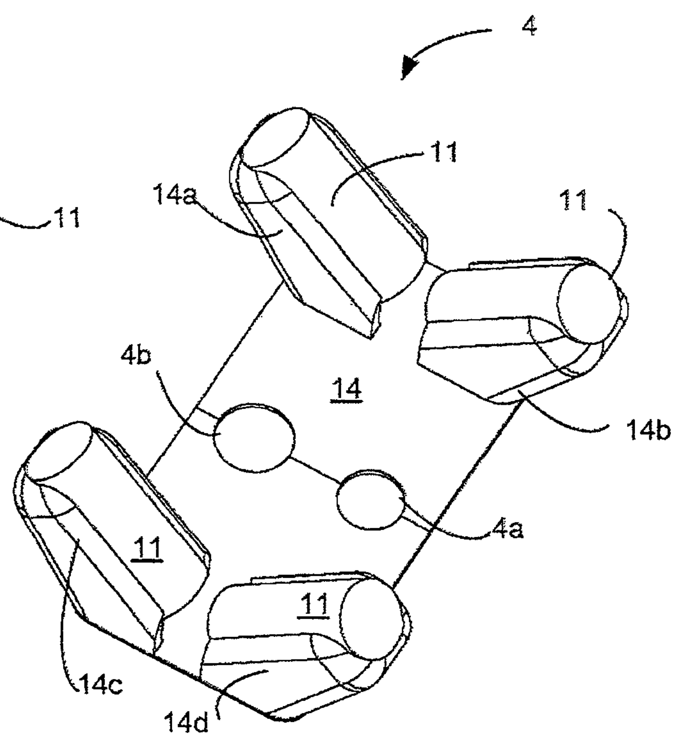
FIG. 14 is a perspective view of FIG. 12 with anti-slip elements inserted to the support top according to one embodiment of the invention.

Referring now to FIGS. 12 and 14, one or more perspective views of the top 4 and its arms 14*a-d*. In one embodiment, each of the arms 14*a-d* may include a flexible anti-slip or non-slip element 11, as further shown in FIG. 13 in a perspective view. In one embodiment, each of the arms 14*a-d* may be cut out to create a cavity 15 to receive the anti-slip element 11. For example, the cavity 15 may be contoured to fit or engage the anti-slip element 11, shown as a cylinder or rod, as the cavity 15 is designed to fit about one half of the circumference of the anti-slip element 11. In another example, the cavity 15 may be less than half of the circumference of that of the anti-slip element 11 so that the anti-slip element 11 may be inserted and held in place as shown in FIG. 14 to provide anti-slip contact with the implement 1 and the arms 14*a-d*. In such an embodiment, the implement 1 may engage or contact exterior surfaces of the anti-slip cylinder rod 11 so that the implement 1 will stay in place without slipping.

In one embodiment, the arms 14*a-d* may not be fitted with the anti-slip cylinder 11. As such, outer edges or surfaces of the arms 14*a-d* may engage the implement 1. Moreover, while the anti-slip element 11 as shown in FIG. 13 is in a shape of a cylinder, it is to be understood that other shapes may be used without departing from the scope or spirit of embodiments of the invention. For example, the anti-slip element 11 may be a layer or surface that is applied onto the arms 14*a-d*. In such an example, the cavity 15 may not be needed.

Moreover, while the arms 14*a-d* may be shown in the figures in a diagonal angle to the base 14, it is to be understood that other configurations may be employed without departing from the scope or spirit of embodiments of the invention. For example, the arms 14*a-d* may be perpendicular to the base 14, but the anti-slip element 11 may be angularly attached or connected to the arms 14*a-d*. In another embodiment, the top 4, with the arms 14*a-d* may be injection-molded and then connected to the handle 3. In another embodiment, the gripping aid 10 may be made as an integral piece.

Figure 15:
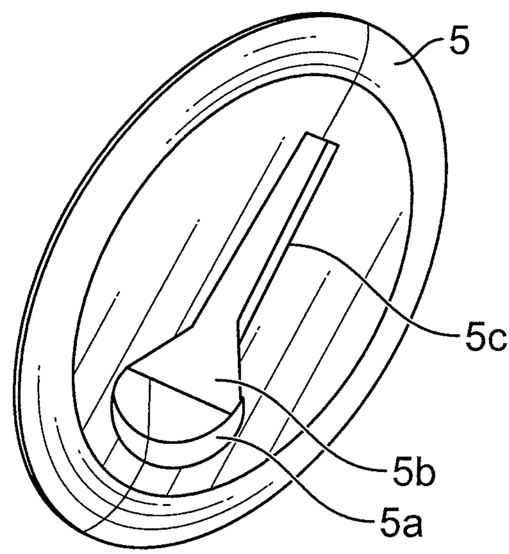
FIG. 15 is a perspective view of a bottom part of a handle without a hand supporting feature according to one embodiment of the invention.
Figure 16:
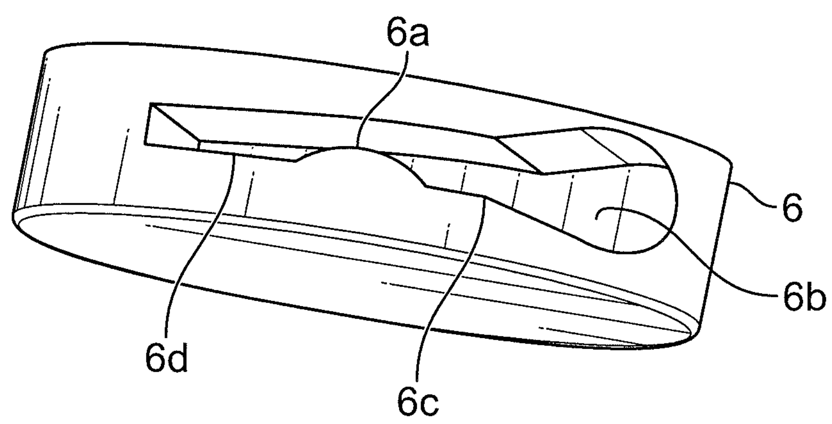
FIG. 16 is a perspective view of a bottom part of a handle with a hand supporting feature according to one embodiment of the invention.

FIG. 15 is a perspective view the end part 5, showing further details of the aperture 5*a*, the "V" shaped portion 5*b*, and the slot 5*c*. FIG. 16 is a perspective view of the bottom 6, as an extension of the end part 5.

It is obvious that the above-described embodiments are merely illustrative of the examples given and are not intended to limit the way it is implemented. It will be apparent to those skilled in the art to make various other changes or variations based on the above description. There is no need and it is not possible to exhaust all the implementation herein. And the obvious changes or variations that have been extended are still within the scope of protection of the present invention.

What is claimed is:

1. A device for manually impaired individuals comprising:

a top element comprising at least two pairs of arms extending outwardly from a base, said base having a first aperture and a second aperture, the top element adapted to removably receive an implement;

an ergonomically shaped handle connecting to the top element, said handle comprising at least one axially extending interior channel and an end part, said end part located at an end of the handle opposite the top element comprising a third aperture connected to a slot by a "V" shaped portion, said third aperture communicating with said axially extending interior channel of said handle;

a restraint comprising a first end attached to at least one of an interior of the handle and the top element, a second end of said restraint extending through the third aperture, the second end selectively engaging with said "V" shaped portion to cinch the restraint, the restraint adapted to restrain the implement against the top element.

2. The device of claim 1, wherein the restraint is exposed outside of the base through the first aperture and the second aperture forming a loop.

3. The device of claim 2, wherein each of the two pairs of arms comprises a surface of the two arms facing each other.

4. The device of claim 3, wherein the loop and the surfaces of each of the two pairs of arms form a space adapted to removably receive and engage the implement.

5. The device of claim 3, further comprising an anti-slip element connected to each of the surfaces.

6. A device for manually impaired individuals comprising:

a top element comprising at least two pairs of arms extending outwardly from a base, said base having a first aperture and a second aperture, the top element adapted to removably receive an implement;

an ergonomically shaped handle connecting to the top element, said handle comprising at least one interior channel and an end part, said endpart comprising a third aperture connected to a slot by a "V" shaped portion;

a restraint comprising a first end attached to an interior of the handle and a second end extending through the third aperture, the second end selectively engaging with said "V" shaped portion to cinch the restraint, the restraint adapted to restrain the implement against the top element;

the first end of the restraint is secured to the interior of the handle by a screw.

7. A device for manually impaired individuals comprising:

a top element comprising at least two pairs of arms extending outwardly from a base, said base having a first aperture and a second aperture, the top element adapted to removably receive an implement;

an ergonomically shaped handle connecting to the top element, said handle comprising at least one interior channels and an end part, said end part comprising a third aperture connected to a slot by a "V" shaped portion;

a restraint comprising a first end attached to an interior of the handle and a second end extending through the third aperture, the second end selectively engaging with said "V" shaped portion to cinch the restraint, the restraint adapted to restrain the implement against the top element;

the first end of the restraint is enclosed within at least one of the interior channels of the handle; and the first end of the restraint is enclosed within at least one of the interior channels of the handle.

8. A device for manually impaired individuals comprising:

a top element comprising at least two pairs of arms extending outwardly from a base, said base having a first aperture and a second aperture, the top element adapted to removably receive an implement;

an ergonomically shaped handle connecting to the top element, said handle comprising at least one interior channels and an end part, said end part comprising a third aperture connected to a slot by a "V" shaped portion;

a restraint comprising a first end attached to an interior of the handle and a second end extending through the third aperture, the second end selectively engaging with said "V" shaped portion to cinch the restraint, the restraint adapted to restrain the implement against the top element;

the second end of the restraint comprises a protuberance having a circumference greater than a circumference of the third aperture, a size of the "V" shaped portion, and a width and a length of the slot.

9. A device for manually impaired individuals comprising:

a top element having a base and at least two pairs of arms extending outwardly from the base, said base comprising a first aperture and a second aperture;

a handle connecting to the top element at a distal end of the top element, said handle having at least one interior channel, the handle comprising an end extension, said end extension comprising a third aperture and a slot connected by a "V" shaped portion at the distal end of the handle;

a restraint comprising a main body, a first end, and a second end, the first end secured to an interior of the handle with the main body of the restraint extending outside of and along a length of the handle and through a fourth aperture in the base, the main body of the restraint entering into the interior of the handle at a fifth aperture of the end extension and exiting at a sixth aperture of the end extension, wherein the second end of the restraint is exposed outside of the handle.

10. The device of claim 9, wherein the main body of the restraint is further exposed outside of the base through the first aperture and the second aperture of the base before exiting at a side aperture in the base, forming a loop exposed outside the handle and between the first aperture and the second aperture.

11. The device of claim 10, wherein each of the two pairs of arms comprises a surface of the two arms facing each other.

12. The device of claim 11, wherein the loop and the surface of each of the two pairs of arms form a space adapted to removably receive and engage an implement.

13. The device of claim 11, further comprising an anti-slip element connected to each of the surfaces of the two pairs of arms.

14. The device of claim 9, wherein the second end of the restraint comprises a protuberance, having a circumference greater than a circumference of the sixth aperture, a size of the "V" shaped portion, and a width and a length of the slot.

15. An apparatus for manually impaired individuals comprising:

a top element comprising at least two pairs of arms extending outwardly from a base, said base having a first aperture and a second aperture, said top element adapted to removably receive an implement;

a handle connecting to the top element, the handle comprising an end part, said end part connected to the handle at an end of the handle opposite the top element, said end part comprising a third aperture connected to a slot in the end part by a "V" shaped portion, said handle having an axially extending hollow interior portion;

a restraint comprising a first end secured to said hollow interior portion of the handle via the first aperture of the base and a second end exposed outside of the handle, the restraint adapted to restrain the implement against the top element.

16. The apparatus of claim 15, wherein each pair of the two pairs of arms comprises a surface on each of the arms facing each other.

17. An apparatus for manually impaired individuals comprising:

a top element comprising at least two pairs of arms extending outwardly from a base, said base having a first aperture and a second aperture, said top element adapted to removably receive an implement;

a handle connecting to the top element, the handle comprising an end part, said end part connected to the handle at an end of the handle opposite the top element, said end part comprising a third aperture connected to a slot in the end part by a "V" shaped portion, said handle having an axially extending hollow interior portion;

a restraint comprising a first end secured to said hollow interior portion of the handle via the first aperture of the base, and a second end exposed outside of the handle, the restraint adapted to restrain the implement against the top element; and an anti-slip element connected to each surface.

18. The apparatus of claim 17, further comprising a cavity in each of the arms removably receiving the anti-slip element.

19. An apparatus for manually impaired individuals comprising:

a top element comprising at least two pairs of arms extending outwardly from a base, said base having a first aperture and a second aperture, said top element adapted to removably receive an implement;

a handle connecting to the top element, the handle comprising an end part, said end part connected to the handle at an end of the handle opposite the top element, said end part comprising a third aperture connected to a slot in the end part by a "V" shaped portion, said handle having an axially extending hollow interior portion;

a restraint comprising a first end secured to said hollow interior portion of the handle via the first aperture of the base, and a second end exposed outside of the handle, the restraint adapted to restrain the implement against the top element; and the restraint forms a loop between the first aperture and the second aperture of the base, the loop and the two pairs of arms adapted to removably receive and secure the implement.

20. A device for manually impaired individuals comprising:

a top element comprising arms extending outwardly from a base, said base having a first aperture and a second aperture, the arms adapted to removably receive and embrace an implement;

a handle connected to the top element, the top element located at a first end of the handle, the handle having at least one axially extending interior channel in the handle;

the at least one axially extending interior channel communicating with a third aperture, said third aperture communicating with a slot in said handle;

a restraint extending through said first and second apertures, a first end of said restraint attached to one of said top element and said handle, said first end of said restraint restrained against movement relative to said top element and said handle;

a second end of said restraint extending through said at least one axially extending interior channel in said handle, said second end of said restraint passing through said third aperture, said second end of said restraint held against axial movement when lodged in said slot.

* * * * *